United States Patent [19]
Matsuno

[11] Patent Number: 5,325,847
[45] Date of Patent: Jul. 5, 1994

[54] DISTAL END PART OF ENDOSCOPE

[75] Inventor: Shinichi Matsuno, Tokyo, Japan

[73] Assignee: Asahi Kogaku Kogyo Kabushiki Kaisha, Tokyo, Japan

[21] Appl. No.: 964,036

[22] Filed: Oct. 21, 1992

[30] Foreign Application Priority Data

Oct. 25, 1991 [JP] Japan .................. 3-278194
Sep. 18, 1992 [JP] Japan .................. 4-249379

[51] Int. Cl.⁵ .............................................. A61B 1/00
[52] U.S. Cl. ............................................. 128/4; 126/6
[58] Field of Search .................... 128/4, 6, 7, 10; 358/98

[56] References Cited

U.S. PATENT DOCUMENTS

| 4,641,635 | 2/1987 | Yabe ............................ 128/6 |
| 4,868,644 | 9/1989 | Yabe et al. .................. 128/6 X |
| 4,971,035 | 11/1990 | Ito ............................. 128/6 |

FOREIGN PATENT DOCUMENTS

| 0219923 | 9/1986 | Japan ......................... 128/6 |
| 62-59914 | 3/1987 | Japan . |
| 0065010 | 3/1987 | Japan ......................... 128/4 |
| 62-66220 | 3/1987 | Japan . |
| 0246715 | 10/1988 | Japan ......................... 128/4 |

Primary Examiner—Richard J. Apley
Assistant Examiner—Beverly A. Meindl
Attorney, Agent, or Firm—Sandler Greenblum & Bernstein

[57] ABSTRACT

A distal end part of an endoscope including an objective optical system which is disposed in the distal end portion of an insert part of the endoscope so that the optical axis of the objective optical system perpendicularly intersects the longitudinal axis of the distal end portion of the insert part. The distal end part further includes a planar image sensor which is incorporated in the distal end portion, so that it can be inserted and removed along the longitudinal axis of the distal end portion. The planar image sensor is secured in opposed relation to the objective optical system to convert an image of an object, which is formed by the objective optical system, into an electric signal.

13 Claims, 7 Drawing Sheets

DISTAL END PART OF ENDOSCOPE

BACKGROUND OF THE INVENTION

The present disclosure relates to subject matter contained in Japanese Patent Application No. 3-278194 (filed on Oct. 25, 1991) and Japanese Patent Application No. 4-249379 (filed on Sep. 18, 1992), which are expressly incorporated herein by reference in their entireties.

1. Field of the Invention

The present invention relates to a distal end part of a side-viewing endoscope having a planar image sensor, such as a solid-state image pickup device, which is incorporated in the distal end portion of an insert part thereof.

2. Description of the Prior Art

The distal end part of a side-viewing endoscope of the type described above has heretofore been arranged with an objective optical system disposed in the distal end portion of the insert part with its optical axis perpendicularly intersecting the longitudinal axis of the insert part distal end portion. A planar image sensor is disposed along the longitudinal axis of the insert part distal end portion, in opposing relation to the objective optical system. The planar image sensor is incorporated in the distal end portion of the insert part, so that it can be inserted and removed in directions perpendicular to the longitudinal axis of the insert part distal end portion (see Japanese Patent Application Laid-Open (KOKAI) No. 62-59914).

In the case of the distal end part of a side-viewing endoscope having a planar image sensor incorporated in the distal end portion of the insert part thereof, if an illuminating light guide fiber bundle 91 is disposed to lie through the space at the back of the planar image sensor 92, as shown in FIG. 9, the limited space can be utilized efficiently, and the diameter of the distal end portion 90 of the insert part can be minimized. Reference numeral 93 in the figure denotes an objective optical system.

However, if the planar image sensor 92 is incorporated in the distal end portion 90, so that it can be inserted and removed in directions (vertically as viewed in FIG. 9) perpendicular to the longitudinal axis of the distal end portion 90, the space at the back of the planar image sensor 92 must be kept vacant as a dead space, and the illuminating light guide fiber bundle 91 must lie through the other portion.

Consequently, the distal end part of the side-viewing endoscope, according to the prior art, which has the planar image sensor 92 incorporated in the distal end portion 90 of the insert part, increases in the diameter, thus intensifying the pain inflicted on the patient, when it is inserted into his/her body cavity.

SUMMARY OF THE INVENTION

An object of the present invention is to provide a distal end part of an endoscope, which is designed so that while a planar image sensor is incorporated in the distal end portion of the insert part, the diameter of the distal end portion is minimized.

Other objects and advantages of the present invention will become apparent from the following detailed description of illustrated embodiments of the invention.

According to the present invention, there is provided a distal end part of an endoscope including an objective optical system which is disposed in the distal end portion of an insert part of the endoscope so that the optical axis of the objective optical system perpendicularly intersects the longitudinal axis of the distal end portion of the insert part. The distal end part further includes a planar image sensor which is incorporated in the distal end portion so that it can be inserted and removed along the longitudinal axis of the distal end portion. The planar image sensor is secured in opposing relation to the objective optical system to convert an image of an object, which is formed by the objective optical system, into an electric signal.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
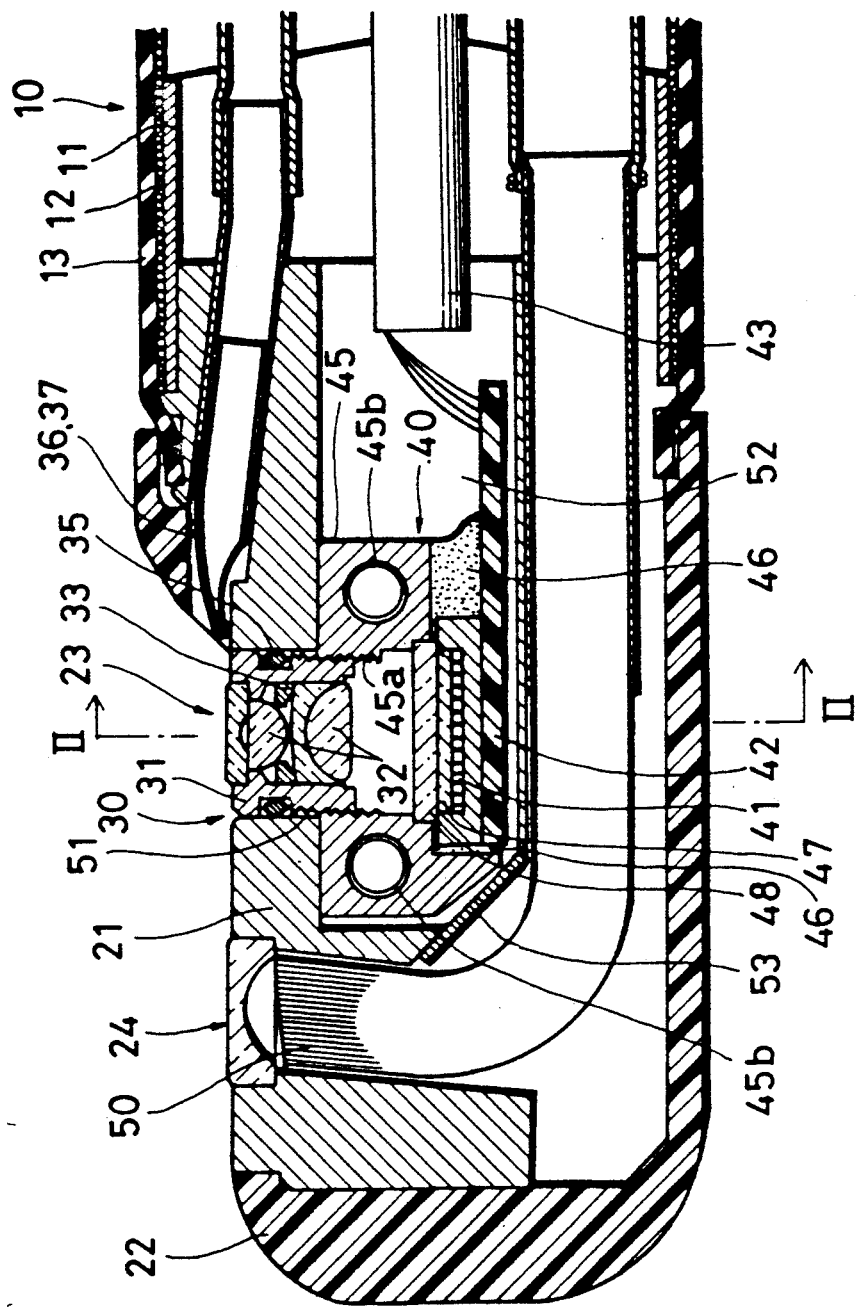
FIG. 1 is a sectional side view of a first embodiment of the present invention.
Figure 2:
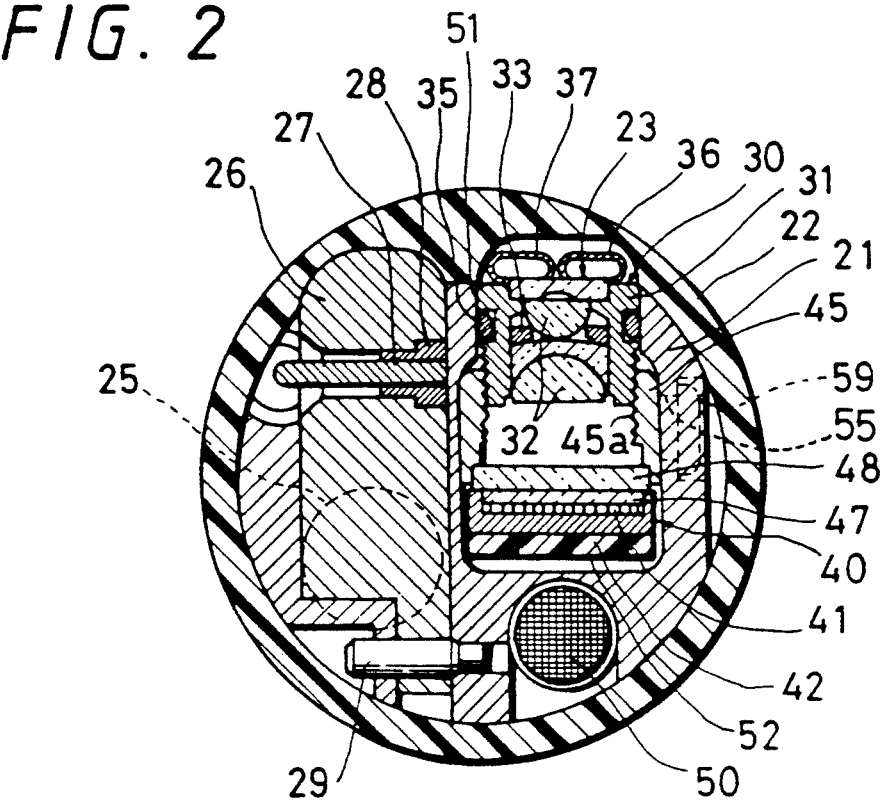
FIG. 2 is a sectional front view (taken along the line II—II in FIG. 1) of the first embodiment of the present invention.

FIGS. 1 to 4 show a first embodiment of the present invention. FIG. 1 is a sectional side view of the distal end portion of an insert part of an endoscope, and FIG. 2 is a sectional view taken along the line II—II in FIG. 1.

The insert part of the endoscope is formed of a flexible tube. A bendable portion 10, which is bendable by remote control, is formed at the distal end of the insert part. Reference numeral 11 denotes a large number of joint rings, which are pivotably connected in series. Reference numerals 12 and 13 denote a braid and a sheathing rubber tube, respectively.

A distal end block 21, which is made of stainless steel, is connected to the distal end of the bendable portion 10. The distal end block 21 is covered with a distal end cover 22, which is made of an electrical insulating plastic material.

A viewing window 23 and an illuminating window 24 are disposed in a side by side relationship in the axial direction of the distal end block 21. A tool guide member 26, for changing the direction of projection of a bioptic forceps or other tool for endoscopy, is disposed in parallel to the two windows 23 and 24, as shown in FIG. 2. The tool guide member 26 extends into a forceps channel 25 and is controlled through a control wire 27, which is secured at one end thereof by a wire securing member 28, so that the control wire 27 will not come off. The tool guide member 26 pivots about a shaft 29.

The objective optical system in this embodiment includes neither a prism nor a mirror. Instead, lens elements of an objective lens 32 are secured in an objective frame 31 in opposing relation to each other with a spacer ring 33 sandwiched therebetween, thereby forming an objective unit 30. The objective unit 30 is disposed in the distal end block 21, so that the optical axis of the unit 30 perpendicularly intersects the longitudinal axis of the distal end block 21.

The outer peripheral surface of the objective frame 31 is formed with a threaded portion and has a sealing O-ring 35 fitted thereon at a position which is closer to the outside than the threaded portion. An air supply nozzle 36 and a water supply nozzle 37 are disposed so as to spout air and water, respectively, toward the surface of the viewing window 23.

A planar image sensor 41 converts an image of the object, which is formed by the objective lens 32, into an electric signal. The planar image sensor 41 is a solid-state image pickup device, for example, a charge coupled device (CCD). The planar image sensor 41 is disposed along the longitudinal axis of the distal end block 21, so as to face the objective lens 32. The planar image sensor 41 is bonded to a substrate 42, to which a cable 43 for signal transmission is connected.

A connecting frame 45 connects together the objective unit 30 and the planar image sensor 41. The connecting frame 45 is bonded to both the planar image sensor 41 and the substrate 42 by using an adhesive 46 in a predetermined positional relationship to the planar image sensor 41. These elements form an image sensor unit 40.

The connecting frame 45 is formed in its center with a relatively large threaded hole 45a which engages with the objective unit 30. The connecting frame 45 is further formed with a pair of relatively small threaded holes 45b for securing it to the distal end block 21, which extend laterally through the forward and rearward end portions, respectively, of the frame 45. The planar image sensor 41 is protected by a cover glass 47. In addition, an optical element 48, e.g., a color compensating filter or a crystal filter, is disposed in close contact with the cover glass 47 of the planar image sensor 41.

The distal end block 21 is provided with an objective receiving hole 51 for inserting the objective unit 30 in a direction perpendicular to the axis of the distal end block 21, and an image sensor receiving hole 52 for inserting the image sensor unit 40 into the distal end block 21 from the rear along the axis of the distal end block 21.

In the distal end block 21, an illuminating light guide fiber bundle 50 lies through the space at the back of the planar image sensor 41, and bends sidewardly so that the exit end of the illuminating light guide fiber bundle 50 faces the inner side of the illuminating window 24. Accordingly, the observational range of the objective lens 32 is illuminated with light that is transmitted through the illuminating light guide fiber bundle 50 and emitted from the exit end thereof. A shading plate 53 prevents leakage of light from the illuminating light guide fiber bundle 50 into the image sensor receiving hole 52.

Figure 3:
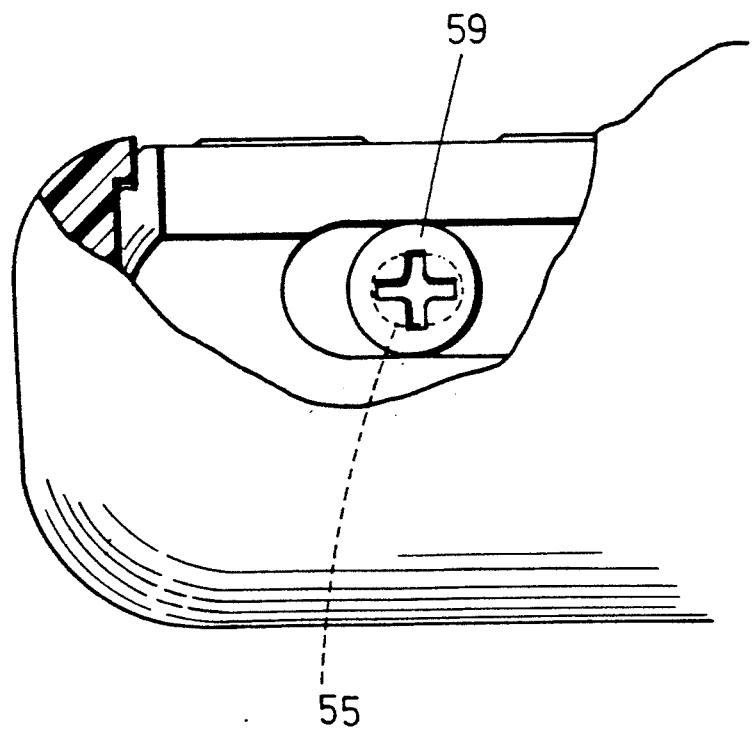
FIG. 3 is a fragmentary side view of the first embodiment of the present invention.

It should be noted that, as shown in FIG. 3, a hole 55 for receiving a screw 59, to secure the connecting frame 45 to the distal end block 21, is elongated in the axial direction of the distal end block 21, so that the connecting frame 45 can be secured to the distal end block 21 in a position determined relative to the distal end block 21.

The optical system in this embodiment, arranged as described above, is incorporated into the distal end block 21, with the objective unit 30 and the image sensor unit 40 assembled as discrete units in advance. The image sensor unit 40 is first inserted into the image sensor receiving hole 52 from the rear of the distal end block 21.

Figure 4:
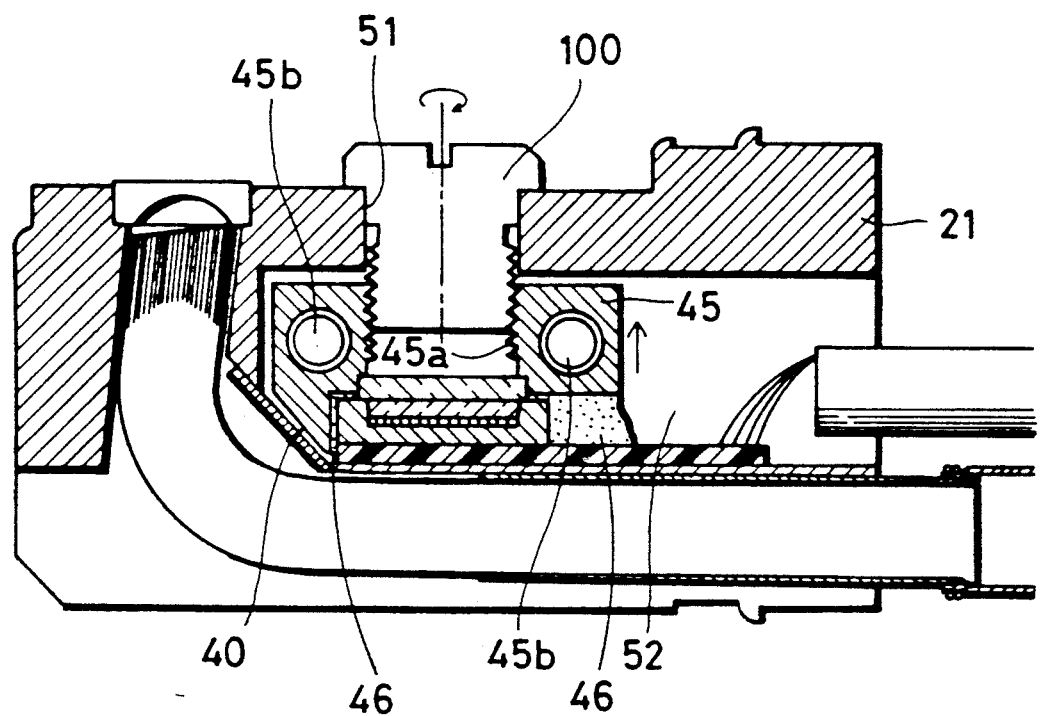
FIG. 4 is a sectional side view showing a process of assembling the first embodiment of the present invention.

Then, as shown in FIG. 4, a jig 100, which is formed with the same external thread as that of the objective frame 31, is inserted into the objective receiving hole 51 and threaded into the large threaded hole 45a provided in the connecting frame 45, thereby setting the connecting frame 45 in a predetermined position. Then, the securing screw 59, which is shown in FIGS. 2 and 3, is threaded into each small threaded hole, provided in the connecting frame 45, thereby securing the connecting frame 45 to the distal end block 21.

Finally, the jig 100 is removed, and the objective unit 30 is threaded into the large threaded hole 45a in the connecting frame 45 through the objective receiving hole 51 in place of the jig 100. After focus adjustment has been made relative to the planar image sensor 41, the objective unit 30 is secured to the distal end block 21. The objective optical system can be detached from the distal end block 21 by reversing the above procedure. However, no jig is needed for the disassembling process.

Figure 5:
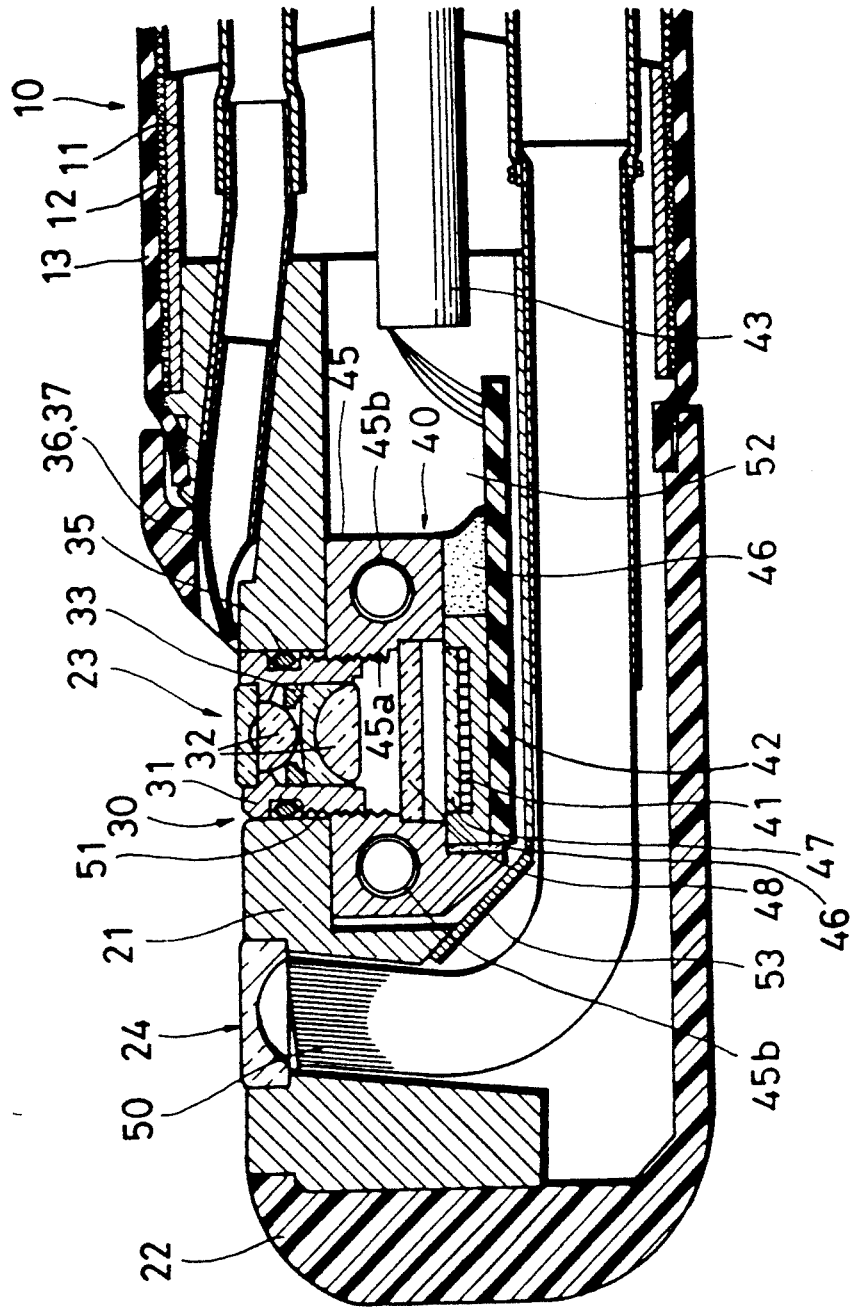
FIG. 5 is a sectional side view of a second embodiment of the present invention.

FIG. 5 shows a second embodiment of the present invention. As illustrated, the optical element 48, e.g., a color compensating filter, or a crystal filter, may be secured to the connecting frame 45 at a position which is separate from the cover glass 47 of the planar image sensor 41.

Figure 6:
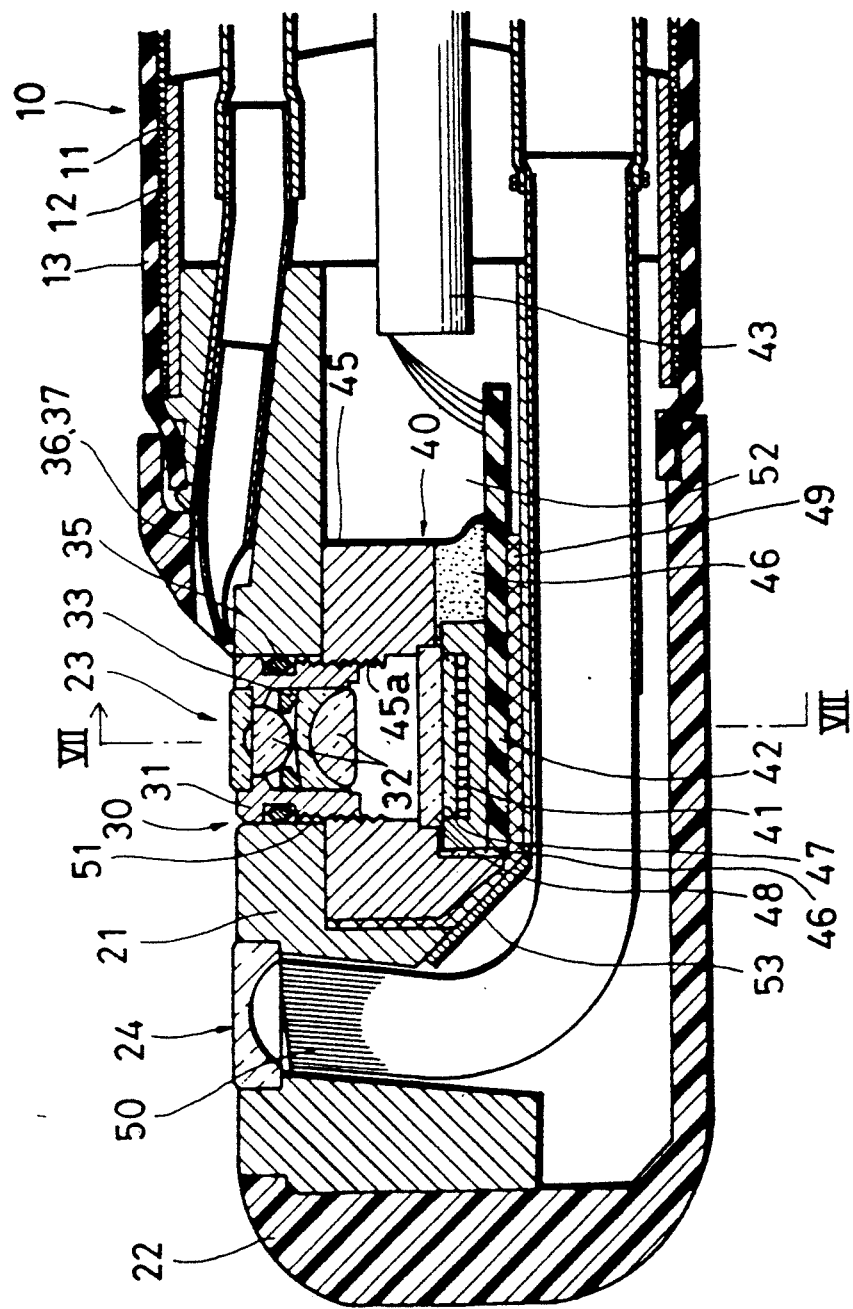
FIG. 6 is a sectional side view of a third embodiment of the present invention.
Figure 7:
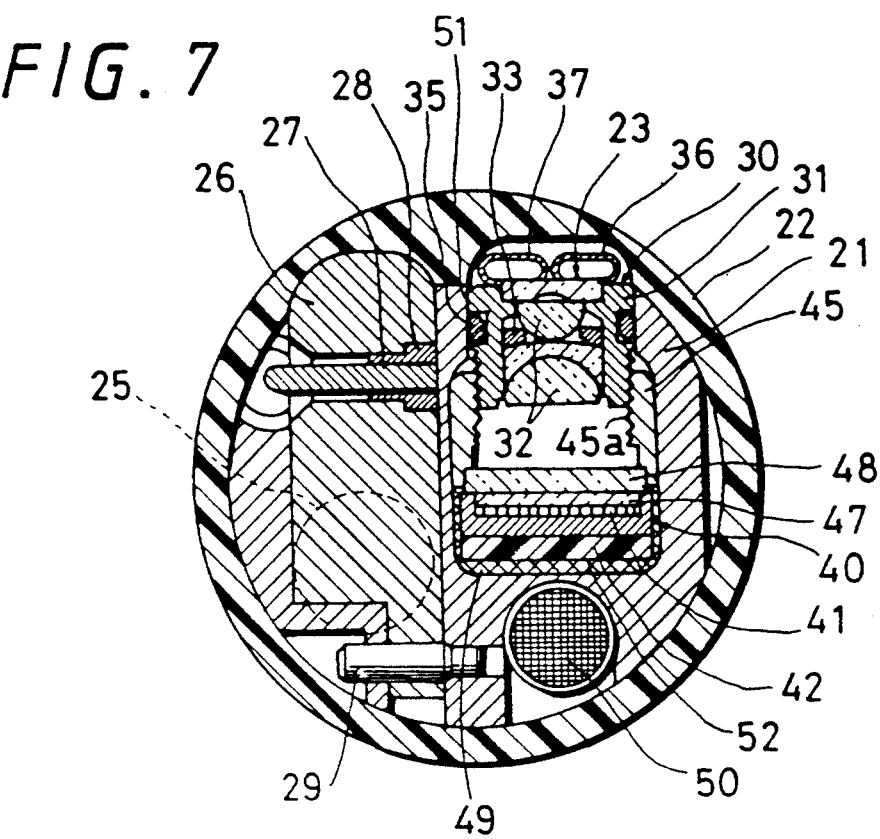
FIG. 7 is a sectional front view (taken along the line VII—VII in FIG. 6) of the third embodiment of the present invention.
Figure 8:
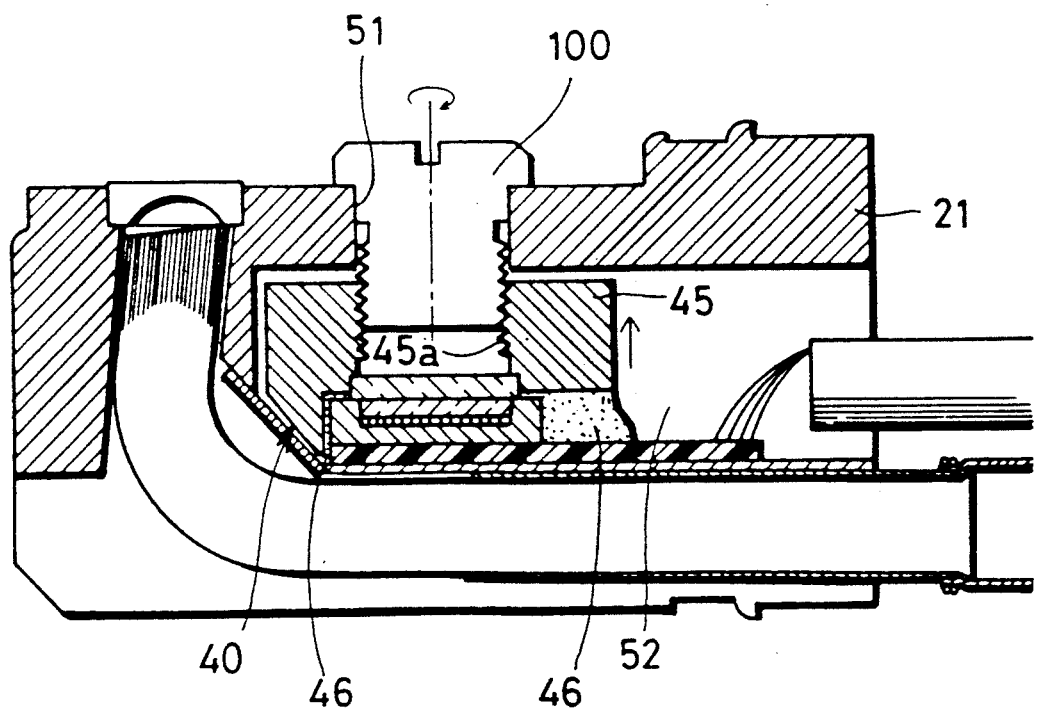
FIG. 8 is a sectional side view showing a process of assembling the third embodiment of the present invention.
Figure 9:
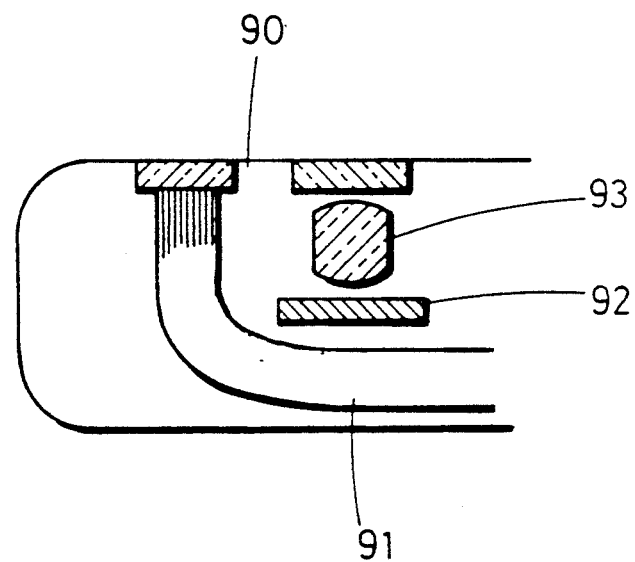
FIG. 9 illustrates schematically one example of a layout in the distal end part of an endoscope.

FIGS. 6 to 8 show a third embodiment of the present invention, in which the connecting frame 45 is secured to the distal end block 21 by using an adhesive and elastic silicone filler 49 without employing the small threaded holes 45b, which are formed in the connecting frame 45 in the first embodiment.

The method of incorporating the optical system into the distal end block 21 in the third embodiment is similar to that in the first embodiment.

The operation of positioning the connecting frame 45 with respect to the distal end block 21 is carried out by inserting the jig 100 into the objective receiving hole 51 and threading it into the relatively large threaded hole 45a, provided in the connecting frame 45, as shown in FIG. 8. Thus, the connecting frame 45 is set at a predetermined position in the distal end block 21.

Subsequently, as shown in FIGS. 6 and 7, the gap between the image sensor unit 40 and the image sensor receiving hole 52 is filled with the silicone filler 49, thereby securing the connecting frame 45 to the distal end block 21.

The use of the filler 49 enables the connecting frame 45 to be secured to the distal end block 21 with flexibility.

Accordingly, even if the cable 43 is pulled strongly when the bendable portion 10 is bent, for example, the connecting frame 45 can tilt flexibly and minutely so as to absorb the movement, thus preventing breakage of the image sensor unit 40.

It should be noted that the operation of assembling the objective unit 30 to the distal end block 21 and the focus adjusting operation are the same as those in the first embodiment.

According to the present invention, the planar image sensor is incorporated in the distal end block so that it can be inserted and removed along the longitudinal axis of the distal end block. Therefore, no dead space is produced at the back of the planar image sensor even in an endoscope wherein the objective optical system is disposed with its optical axis perpendicularly intersecting the longitudinal axis of the distal end portion of the insert part. The planar image sensor is disposed along the longitudinal axis of the insert part distal end portion in opposing relation to the objective optical system. Accordingly, the illuminating light guide fiber bundle or other associated element can be efficiently disposed in the space at the back of the planar image sensor. Thus, the diameter of the distal end block can be minimized.

While the invention has been described by reference to specific embodiments chosen for purposes of illustration, it should be apparent that numerous modifications could be made thereto by those skilled in the art without departing from the basic concept and scope of the invention.

I claim:

1. A distal end part of an endoscope comprising:
   a distal end block in said distal end part of said endoscope, said distal end block having a first hole extending perpendicularly to a longitudinal axis of said distal end block and a second hole extending along said longitudinal axis;
   an objective optical system which is disposed in said first hole of said distal end block, so that an optical axis of said objective optical system perpendicularly intersects said longitudinal axis of said distal end block; and
   a planar image sensor incorporated in said second hole of said distal end block along the longitudinal axis of said distal end block, and secured in opposing relation to said objective optical system to convert an image of an object, which is formed by said objective optical system, into an electric signal.

2. A distal end part of an endoscope according to claim 1, wherein said objective optical system is free of a prism and a mirror.

3. A distal end part of an endoscope according to claim 1, wherein said planar image sensor is a charge coupled device.

4. A distal end part of an endoscope according to claim 1, further comprising a connecting frame for connecting together said objective optical system and said planar image sensor in a predetermined positional relationship, wherein an objective frame of said objective optical system and said planar image sensor are secured to said connecting frame, and said distal end block receiving said objective frame, said connecting frame being separate from said distal end block.

5. A distal end part of an endoscope according to claim 4, wherein said connecting frame is secured to said distal end block by a screw.

6. A distal end part of an endoscope according to claim 4, wherein said connecting frame is secured to said distal end block by an adhesive and elastic filler.

7. A distal end part of an endoscope according to claim 4, wherein said planar image sensor is bonded to said connecting frame by an adhesive.

8. A distal end part of an endoscope according to claim 4, wherein said objective frame of said objective optical system is threaded into said connecting frame sidewardly.

9. A distal end part of an endoscope according to claim 4, wherein said second hole allows inserting and removing both said connecting frame and said planar image sensor from said distal end portion, and said first hole allows inserting and removing said objective frame form a side of said distal end block.

10. A distal end part of an endoscope according to claim 1, further comprising a light guide fiber bundle for transmitting light for illuminating an observational range of said objective optical system, said light guide fiber bundle being disposed in said distal end portion, and lying through a space extending along the length of said planar image sensor.

11. A method for assembling a distal end part of an endoscope, said distal end part including an objective optical system, a planar image sensor, and a distal end block having a front and rear, the method comprising the steps of:
   inserting said planar image sensor into said distal end block from the rear and along a longitudinal axis of said distal end block toward the front; and
   inserting said objective optical system into said distal end block in a direction perpendicular to the longitudinal axis of said distal end block.

12. A method for assembling a distal end part of an endoscope according to claim 11, wherein said distal end block includes a first hole and a second hole, said objective optical system being inserted into said first hole, and said planar image sensor being inserted into said second hole.

13. A method for assembling a distal end part of an endoscope according to claim 11, further comprising securing said objective optical system and said planar image sensor to a connecting frame, said connecting frame being secured to said distal end block.

* * * * *